United States Patent [19]
Fuisz et al.

[11] Patent Number: 5,654,003
[45] Date of Patent: Aug. 5, 1997

[54] PROCESS AND APPARATUS FOR MAKING TABLETS AND TABLETS MADE THEREFROM

[75] Inventors: Richard C. Fuisz, Great Falls, Va.; Subraman R. Cherukuri, Towaco, N.J.

[73] Assignee: Fuisz Technologies Ltd., Chantilly, Va.

[21] Appl. No.: 194,682

[22] Filed: Feb. 10, 1994

Related U.S. Application Data

[63] Continuation-in-part of Ser. No. 847,595, Mar. 5, 1992, Pat. No. 5,387,431, and Ser. No. 881,612, May 12, 1992, abandoned, which is a continuation of Ser. No. 120,171, Sep. 10, 1993, Pat. No. 5,501,858.

[51] Int. Cl.$^6$ .................... A61K 9/26; A61K 9/68
[52] U.S. Cl. .......... 424/469; 424/464; 424/440; 424/439; 514/951; 514/965
[58] Field of Search ................. 424/464–469, 424/479, 401, 439, 440, 441; 514/951, 965

[56] References Cited

U.S. PATENT DOCUMENTS

| | | | |
|---|---|---|---|
| 2,826,169 | 3/1958 | Le Veen | 119/1 |
| 3,019,745 | 2/1962 | Du Bois et al. | 107/8 |
| 3,036,532 | 5/1962 | Bowe | 107/8 |
| 3,067,743 | 12/1962 | Merton et al. | 128/270 |
| 3,070,045 | 12/1962 | Bowe | 107/8 |
| 3,073,262 | 1/1963 | Bowe | 107/8 |
| 3,095,258 | 6/1963 | Scott | 18/54 |
| 3,118,396 | 1/1964 | Brown et al. | 107/8 |
| 3,131,428 | 5/1964 | Mika | 18/8 |
| 3,308,221 | 3/1967 | Opfell | 264/174 |
| 3,482,998 | 12/1969 | Carroll et al. | 99/108 |
| 3,523,889 | 8/1970 | Eis | 210/20 |
| 3,557,717 | 1/1971 | Chivers | 107/54 |
| 3,595,675 | 7/1971 | Ash et al. | 99/130 |
| 3,615,671 | 10/1971 | Schoaf | 99/78 |
| 3,625,214 | 12/1971 | Higuchi | 128/260 |

(List continued on next page.)

FOREIGN PATENT DOCUMENTS

| | | |
|---|---|---|
| 609135 | 4/1988 | Australia . |
| 609137 | 4/1988 | Australia . |
| 900605 | 11/1977 | Belgium . |
| 1303511 | 4/1988 | Canada . |
| 0 287 488 A1 | 3/1988 | European Pat. Off. . |
| 0 387 950 A1 | 8/1990 | European Pat. Off. . |
| 86052 | 4/1988 | Israel . |
| 86053 | 4/1988 | Israel . |
| 88/277 | 4/1988 | South Africa . |
| 88/2770 | 4/1988 | South Africa . |
| 89/9318 | 12/1989 | South Africa . |
| 90/2139 | 3/1990 | South Africa . |
| 90/8406 | 8/1991 | South Africa . |
| 489211 | 7/1968 | Switzerland . |
| 519858 | 5/1971 | Switzerland . |
| 2 155 934 | 3/1985 | United Kingdom . |
| WO91/18613 | 5/1991 | WIPO . |

OTHER PUBLICATIONS

*The Merck Index*, 1989 p. 465.

R.H. Doremus, "Crystallization of Sucrose From Aqueous Solution," *Journal of Colloid and Interface Science*, 104, pp. 114–120 (1985).

P. Bennema, "Surface Diffusion and Growth of Sucrose Crystals," *Journal of Crystal Growth*, 3,4 pp. 331–334 (1968).

T.D. Simpson, et al., "Crystalline Forms of Lactose Produced in Acidic Alcoholic Media," *Journal of Food Science*, 47, pp. 1948–1954 (1982).

A.D. Randolph, et al., "Continuous Sucrose Nucleation", *The International Sugar Journal*, pp. 8–12 (1974).

(List continued on next page.)

*Primary Examiner*—Sallie M. Gardner
*Attorney, Agent, or Firm*—Hoffmann & Baron

[57] ABSTRACT

The present invention is a process for making edible units from compression and the products resulting therefrom. The method of the present invention includes compression of shearform matrix mass sufficiently to form a comestible compression unit such as a compression tablet.

15 Claims, 6 Drawing Sheets

U.S. PATENT DOCUMENTS

| | | | |
|---|---|---|---|
| 3,676,148 | 7/1972 | De Weese et al. | 99/1 |
| 3,686,000 | 8/1972 | Lawrence | 99/134 R |
| 3,723,134 | 3/1973 | Chivers | 99/134 |
| 3,762,846 | 10/1973 | Chivers | 425/7 |
| 3,856,443 | 12/1974 | Salvi | 425/9 |
| 3,875,300 | 4/1975 | Homm et al. | 424/28 |
| 3,876,794 | 4/1975 | Rennhard | 426/152 |
| 3,925,525 | 12/1975 | LaNieve | 264/40 |
| 3,930,043 | 12/1975 | Warning et al. | 426/515 |
| 3,951,821 | 4/1976 | Davidson | 252/1 |
| 3,967,623 | 7/1976 | Butterworth et al. | 128/287 |
| 3,972,725 | 8/1976 | Nicol | 127/58 |
| 3,981,739 | 9/1976 | Dmitrovsky et al. | 127/60 |
| 3,992,265 | 11/1976 | Hansen | 195/127 |
| 4,056,364 | 11/1977 | Dmitrovsky | 23/273 |
| 4,086,414 | 4/1978 | Turbak et al. | 536/30 |
| 4,090,920 | 5/1978 | Studer, Jr. | 195/127 |
| 4,136,145 | 1/1979 | Fuchs et al. | 264/164 |
| 4,153,512 | 5/1979 | Messner et al. | 195/103.5 |
| 4,159,210 | 6/1979 | Chen et al. | 127/29 |
| 4,293,570 | 10/1981 | Vadasz | 426/3 |
| 4,303,684 | 12/1981 | Pitchon et al. | 426/312 |
| 4,338,350 | 7/1982 | Chen et al. | 426/658 |
| 4,348,420 | 9/1982 | Lynch et al. | 426/772 |
| 4,362,757 | 12/1982 | Chen et al. | 426/599 |
| 4,371,516 | 2/1983 | Gregory et al. | 424/22 |
| 4,376,743 | 3/1983 | Dees | 264/103 |
| 4,382,963 | 5/1983 | Klose et al. | 426/3 |
| 4,492,685 | 1/1985 | Keith et al. | 424/28 |
| 4,496,592 | 1/1985 | Kuwahara et al. | 424/5 |
| 4,500,546 | 2/1985 | Turbak et al. | 514/781 |
| 4,504,509 | 3/1985 | Bell | 426/549 |
| 4,511,584 | 4/1985 | Percel et al. | 426/99 |
| 4,526,525 | 7/1985 | Oiso et al. | 425/9 |
| 4,585,797 | 4/1986 | Cioca | 514/773 |
| 4,619,833 | 10/1986 | Anderson | 426/548 |
| 4,765,991 | 8/1988 | Cherukuri et al. | 426/3 |
| 4,772,477 | 9/1988 | Weiss et al. | 426/99 |
| 4,793,782 | 12/1988 | Sullivan | 425/7 |
| 4,855,326 | 8/1989 | Fuisz | 514/777 |
| 4,872,821 | 10/1989 | Weiss | 425/9 |
| 4,873,085 | 10/1989 | Fuisz | 424/400 |
| 4,879,108 | 11/1989 | Yang et al. | 424/440 |
| 4,885,281 | 12/1989 | Hanstein et al. | 514/53 |
| 4,978,537 | 12/1990 | Song | 426/5 |
| 4,997,856 | 3/1991 | Fuisz | 514/777 |
| 5,011,532 | 4/1991 | Fuisz | 106/215 |
| 5,028,632 | 7/1991 | Fuisz | 514/772 |
| 5,034,421 | 7/1991 | Fuisz | 514/772 |
| 5,073,387 | 12/1991 | Whistler | 426/7 |
| 5,082,684 | 1/1992 | Fung | 426/602 |
| 5,084,295 | 1/1992 | Whelan et al. | 426/565 |
| 5,089,606 | 2/1992 | Cole et al. | 536/54 |
| 5,094,872 | 3/1992 | Fursik et al. | 426/578 |
| 5,096,492 | 3/1992 | Fuisz | 106/215 |
| 5,173,322 | 12/1992 | Melachouris | 426/580 |
| 5,196,199 | 3/1993 | Fuisz | 424/401 |
| 5,236,734 | 8/1993 | Fuisz | 426/641 |
| 5,238,696 | 8/1993 | Fuisz | 426/565 |
| 5,279,849 | 1/1994 | Fuisz et al. | 426/658 |

OTHER PUBLICATIONS

K.B. Domovs, et al., "Methanol–Soluble Complexes of Lactose and of other Carbohydrates," *J. Dairy Science*, 43, pp. 1216–1223 (1960).

A.D. Randolph, et al., "Continuous Sucrose Nucleation", *The International Sugar Journal*, pp. 35–38 (1974).

A.D. Randolph, et al., "Continuous Sucrose Nucleation" *The International Sugar Journal*, pp. 73–77 (1974).

ICI Americas Inc., "ICI Americas Products for Cosmetics and Pharmaceuticals", (1977).

Domino Sugar Corporation, "Co–crystallization". (undated).

Domino Sugar Corporation, "Raspberry". (undated).

Domino Sugar Corporation, "Molasses Dark". (undated).

FIG-6a
FIG-6b
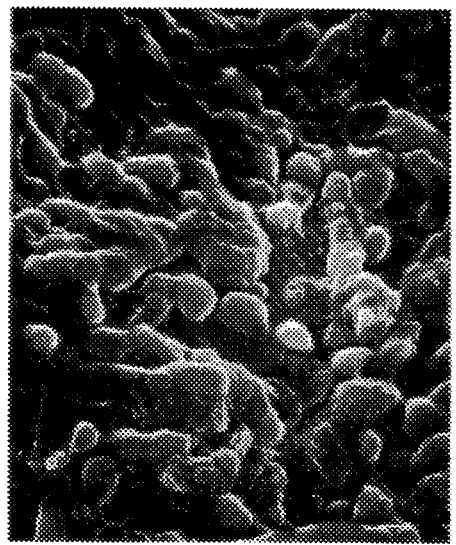
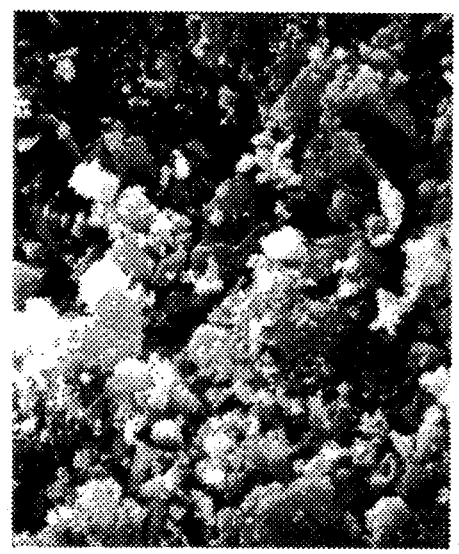

PROCESS AND APPARATUS FOR MAKING TABLETS AND TABLETS MADE THEREFROM

The present application is a continuation in part application of U.S. application Ser. No. 07/847,595 filed Mar. 5, 1992, which issued as U.S. Pat. No. 5,387,431 on Feb. 7, 1995, and U.S. application Ser. No. 07/881,612, now abandoned, filed May 12, 1992, which was subsequently refiled as continuation application bearing U.S. Ser. No. 08/120,171 on Sep. 10, 1993, now U.S. Pat. No. 5,501,858 issued Mar. 26, 1996.

BACKGROUND OF THE INVENTION

The present invention relates to the art of making comestibles, such as tablets, by compression.

Compressed tablets are prepared by compressing a formulation containing a medicinal substance or drug and other ingredients, such as excipients selected for properties which enhance the production and use of the tablet. There are currently three known basic methods for preparing tablet granulations. These are wet granulation, dry granulation and direct compression. Both wet and dry granulations involve the formation of an agglomerate for feeding to a die cavity. Direct compression usually involves compressing a powder blend of an active ingredient with suitable excipients.

The preparation of formulations for tabletting by wet granulation is the oldest method and still the most widely used. Wet granulation involves many steps, including: milling of drugs and excipients, mixing of the milled powders, preparation of binder solution, mixing of binder solution with powder mixture to form a wet mass, coarse screening of the wet mass using 6–12 mesh screens, drying of moist granules, screening of dry granules through 14–20 mesh screen, mixing of screen granules with lubricant and disintegrant, and tablet compression.

Wet granulation is an expensive process because it requires many processing steps and involves considerable material handling equipment. Consequently, the process requires both energy and substantial space which should be environmentally controlled.

Dry granulation refers to the granulation of a powder mixture by compression without the use of heat and solvent. Dry granulation is used when wet granulation is not available because the drug is sensitive to moisture or heat.

Two methods are used for dry granulation. One method is slugging, where the powder is precompressed on a heavy-duty tablet press, and the resulting tablets or slugs are milled to yield the granulation. The other method is precompression of the powder with pressure rolls using a compactor.

Dry granulation has many disadvantages. It requires a specialized heavy-duty tablet press to form the slug; it does not permit uniform color distribution as can be achieved with wet granulation, where dye can be incorporated into the binder liquid; the pressure roll press cannot be used with insoluble drugs because this may retard the dissolution rate; and the process tends to create dust thereby increasing the potential for cross-contamination.

Direct compression tabletting has the least amount of steps. Direct compression is used in a process by which tablets are compressed directly from powder blends of the active ingredient and suitable excipients (including fillers, disintegrants, and lubricants) which are included in the mix to provide uniform flow into the die cavity and form a firm solid compression tablet. No pretreatment of the powder blends by wet or dry granulation procedures is necessary.

Although it has considerably fewer steps than either wet or dry granulation processes, direct compression also has many technological limitations. These limitations include primarily obtaining sufficient flow, and obtaining bonding of particles to form a strong compressed tablet. Low-dose drugs are difficult to blend, that is, uniform distribution of the drug is not easily attained and unblending sometimes occurs during the compression stage. High-dose drugs do not lend themselves to direct compression because of poor flowability and poor compressibility. A typical example would be some of the antacid drugs, such as aluminum hydroxide and magnesium carbonate.

When direct compression is used the choice of excipients is extremely critical. It is desirable that when using direct compression fillers and binders possess both compressibility and fluidity. In addition to compressibility failures, the process of direct compression also has disadvantages in the area of blending. Direct compression blends are subject to unblending in post blending handling steps. Differences in particle size because of differences in density between drug and excipient particles may also lead to unblending in the hopper or feedframe on the tablet press.

A disadvantage of all prior art process is the production of fines usually associated with making compression tablets. In the prior art, preparation of particles for formulation of tablets by compression results in a noticeable amount of fines, i.e., very tiny particles on the order of 150 microns and less. These fines can interfere with operation of apparatus for feeding tabletting machines as well as the operation of the tabletting machines. Often, it is necessary to conduct tablet production in a facility which is environmentally controlled to eliminate or reduce the fines. This adds to the cost of production of the tablets.

Moreover, a percentage of the non-compressed particulate is lost during production because there are fines dispersed and cannot be recaptured, and because some of the fines are not capable of being recovered for recycle.

It is desirable to design a method for making compression tablet delivery systems which includes advantages of wet and dry granulation and direct compression but does not have the disadvantages associated therewith. The present inventor has several patents which relate to, among other things, unique delivery means.

For example, in U.S. Pat. No. 4,855,326 to Fuisz, the inventor has previously disclosed that a fiber form of medicament-bearing product can be compacted to form a sheet-like body. He cautions, however, that the compact body cannot be squeezed too much for fear of breaking the fibrous mass. There is no indication to form a compressed tablet as a medicinal dosage form.

Similarly, in U.S. Pat. No. 4,873,085 a spun fibrous cosmetic is disclosed as well as a compacted form of sugar fibers to form a sheet-like body which can be handled more readily. There is no indication to form a compressed tablet.

In U.S. Pat. No. 4,997,856, a wafer-like structure is disclosed in which a medicament is distributed on or through spun fibers which are then chopped by passing through a conventional "food grinder" (Hobart hamburger grinder). The enclosed volume of the end product is less than 30%, and preferably less than 15%, of the as-spun volume of floss. There is no mention in the '856 disclosure to form a compressed tablet.

The use of compacted spun fibers in the same sense as in the patents mentioned above is also disclosed in U.S. Pat. Nos. 5,034,421 and 5,096,492. None of these disclosures suggest formation of a compressed tablet.

It is, therefore, an object of the present invention to overcome or ameliorate the disadvantages existing in the previous methods of preparing compression tablets. A further object of the present invention is to produce an improved compression tablet.

Other and further objects will be realized by those skilled in the art in view of the following disclosure.

SUMMARY OF THE INVENTION

The present invention includes a method of making a solid comestible, such as a tablet, which includes compressing shearform matrix masses sufficiently to form a comestible compression unit.

The masses of shearform matrix can be formed by subjecting a feedstock material to flash-flow conditions so that the feedstock can be transformed to deformable randomly-shaped and randomly-sized particles which are compressible.

The flash-flow conditions can be provided by high speed spinning the feedstock in a spinning head wherein the material is subjected to high shear sufficient to create flash-flow and which discharges the masses during spinning. Alternatively, it is presently known that flash-flow can be provided by heating feedstock in a non-solubilized condition sufficiently to provide internal flow conditions, and then subjecting the feedstock to sufficient fluid shear force and disrupt the feedstock to form the masses.

The feedstock preferably includes a carrier material which undergoes morphological transformation during flash-flow processing to produce the matrix. In a preferred embodiment, the feedstock also includes an additive which, during flash-flow processing, is mixed and microstructurally stabilized in the matrix.

Additives contemplated for use in the present invention include medicaments, dyes, fragrances, sweeteners, flavors, fillers, binders, lubricants, disintegrants, and mixtures thereof. In a most preferred embodiment, the additive is a medicament which is an antacid.

The present method can be used to make a compression product without the requirement of a processing aid such as a flow agent, binder, disintegrant, etc. Such aids can be included, however, to obtain certain desired product characteristics and processing improvements.

The product of the present invention is unique in that it possesses microstructurally stabilized components. These components are rendered microstructurally stabilized by flash-flow processing. Consequently, compression formation of the product can be performed directly after flash-flow processing. No other processing steps are required.

"Microstructural stabilization" as used herein means a unique characteristic achieved by mixing and morphologically transforming the feedstock into shear form masses. The term microstructurally stabilized does not mean rigidly fixed in place geometrically, but rather firmly frozen into the matrix with respect to other components processed by flash-flow. The matrix, in turn, is deformable under compression but the components are locked into place with respect to each other. A detailed description and further elucidation of this concept shall be set forth in the detailed description and the drawings.

As a further feature of this unique process, the body of the compressed unit includes disintegratable interstices which enhance disintegration into particles while also improving the wettability of the separate particles.

The present invention also includes an apparatus for manufacturing a compression comestible such as a tablet.

The apparatus of the present invention includes flash-flow apparatus for forming shearform matrix masses. The other required component for the present invention is a compression tablettor having at least one dye cavity and compression punch. The compression tablettor is connected to the flash-flow apparatus for transfer of shearform matrix masses from the flash-flow apparatus to the die cavity or cavities for compression formation of a tablet. The flash-flow apparatus as presently known can include either a free form melt spinning apparatus wherein free form agglomerates are formed, or an apparatus for forming shearform matrix by impinging high fluid force on an extruded mass of material during internal flow condition.

As a result of the invention, a new product is provided which is readily disintegratable into particles which have enhanced wettability characteristics.

Furthermore, as a result of the present invention, the non-uniformity of mixture resulting in prior direct compression processes has been overcome. This is achieved by "fuse and compression" steps of the present invention. Moreover, energy and space requirements of wet and dry granulation are overcome. Furthermore, the advantages of direct compression are obtained using an agglomerate rather than a powder which must be maintained in a highly mixed and free flow condition to obtain the desired results.

Yet another advantage is the virtual elimination of fines associated with tablet making. Consequently, the requirements for handling the fines, for recovery and recycle of fines, and the loss of material resulting from fines are eliminated.

These and other advantages of the present invention will be appreciated from the examples which are set forth herein to elucidate the understanding of the invention, but which are not intended in any way to limit the scope thereof.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein:

FIGS. 6(a) and 6(b) are photomicrographs of an invention tablet at 6(a) and a prior art tablet at 6(b) taken at magnification of 1,090 and 1,000, respectively.

DETAILED DESCRIPTION OF THE INVENTION

The present invention includes a method of making a compression tablet. The tablet possesses a rigid structure and a surface which has hardness, i.e., resists penetration and deformation. In the prior art, compression tablets are produced by high pressure compression. High pressure is needed to intimately bind the particles of the tablet together.

The present invention improves the art of tabletting because it reduces the requirement of high compression to form tablets, and because the tablets prepared thereby possess a consistent homogeneous mixture of tablet components. Moreover, the process is improved so that certain drawbacks associated with the prior art, such as multiple steps and production of fines, are reduced or eliminated.

Tabletting machines useful for preparing compression tablets usually include a die and a punch. Feeding mechanisms direct the granulation to the die cavity and punches compress the tablet once the granulation has been placed in the die cavity. The tablet press may be a single station (or single punch press) or, alternatively, a multistation rotary press.

The material which is fed to the tabletting machine in the present invention is a free-form agglomerate in which the selected ingredients, such as a medicinal substance, and a carrier material are fused together. The free-form agglomerate is distinguished from agglomerates formed from wet and dry granulations.

Figure 2A:
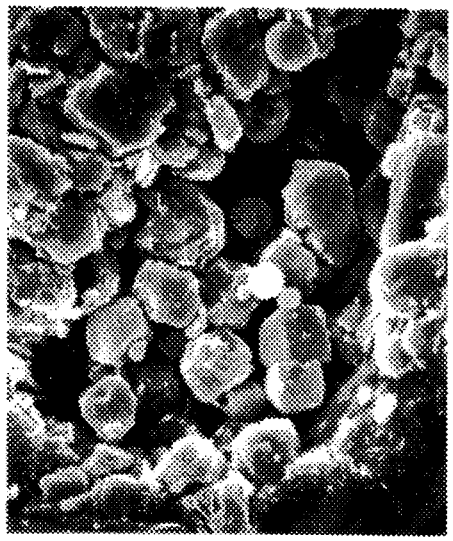
FIGS. 2(a) and 2(b) are photomicrographs comparing the structure of a compression antacid tablet made according to the present invention with a prior art compression antacid tablet.

In the present invention, the components of the tablet are thoroughly dispersed throughout the product because the mixture attained in the free-form agglomerate is microstructurally stabilized against migration out of mixture. This unique capability has been demonstrated by reference to FIGS. 2(a) and 2(b). In FIG. 2(a), a photomicrograph taken at 1,000 magnification shows the cross section of a compression tablet formed in accordance with the process of the present invention. It is significant to note that the particles shown therein each contained components which are microstructurally stabilized or "frozen" with respect to each other in spite of the compression step to which they have been subjected. In direct contrast thereto, the photomicrograph shown at FIG. 2(b) displays at 1,000 magnification the cross section of a compression tablet in which individual components are indiscriminently "clumped" and are not microstructurally frozen with respect to each other.

Figure 2B:
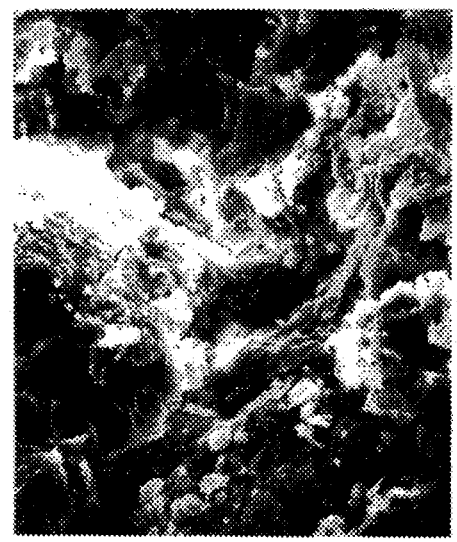
Figure 3B:
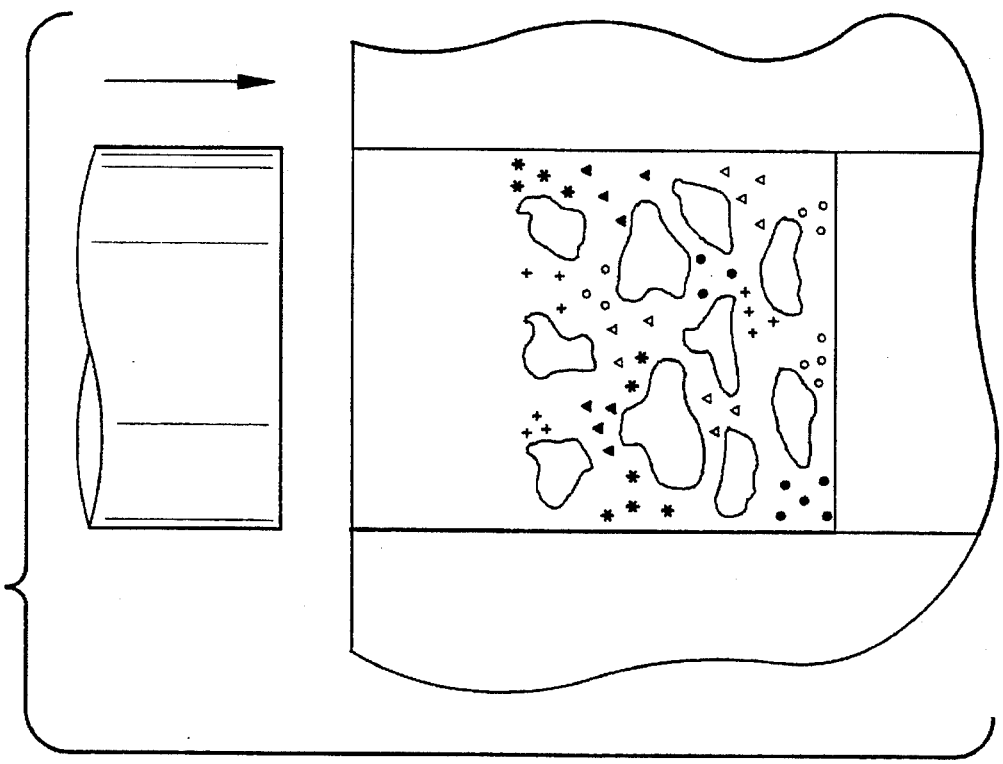
FIG. 3(b) is a schematic representation of a compression die filled with pre-compression particles for a tablet prepared in accordance with the prior art.
Figure 3A:
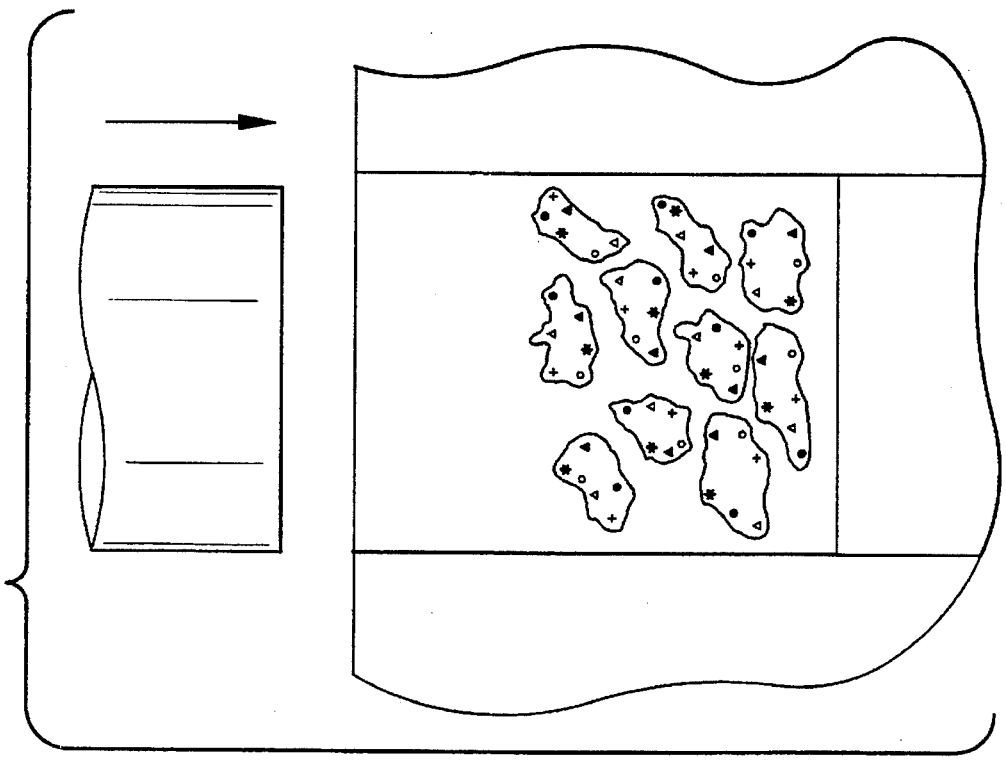
FIG. 3(a) is a schematic representation of a compression die filled with pre-compression particles prepared in accordance with the present invention.

The phenomenon showed at FIGS. 2(a) and 2(b) are explained by references to FIGS. 3(a) and 3(b) and FIGS. 4(a) and 4(b). In particular, in FIG. 3(a), the free-form agglomerates are shown after they have been fed into a compression die. In FIG. 3(b) pre-compression components of a tablet which have not been subjected to shearform processing are depicted in a die. Consequently, the ingredients are not microstructurally frozen in free-form agglomerates. In each case, there are basically six components represented by *''s, +'s, Δ's, ▲'s, o's, and ●'s. In FIG. 3(a), each of the components are microstructurally stabilized or frozen with respect to each other while in FIG. 3(b) the components are subject to separation as a result of the feeding mechanisms which direct the particles into the die cavity. The components are not microstructurally fixed with respect to each other and can agglomerate in "clumps of components" as displayed in FIG. 3(b).

Figure 4B:
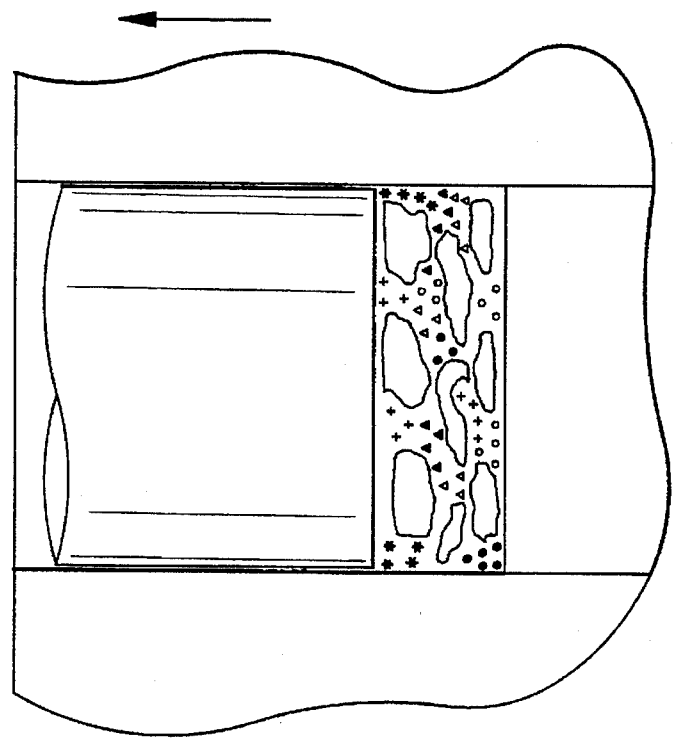
FIG. 4(b) is a schematic representation of a compression die during compression of a tablet prepared in accordance with the prior art.
Figure 4A:
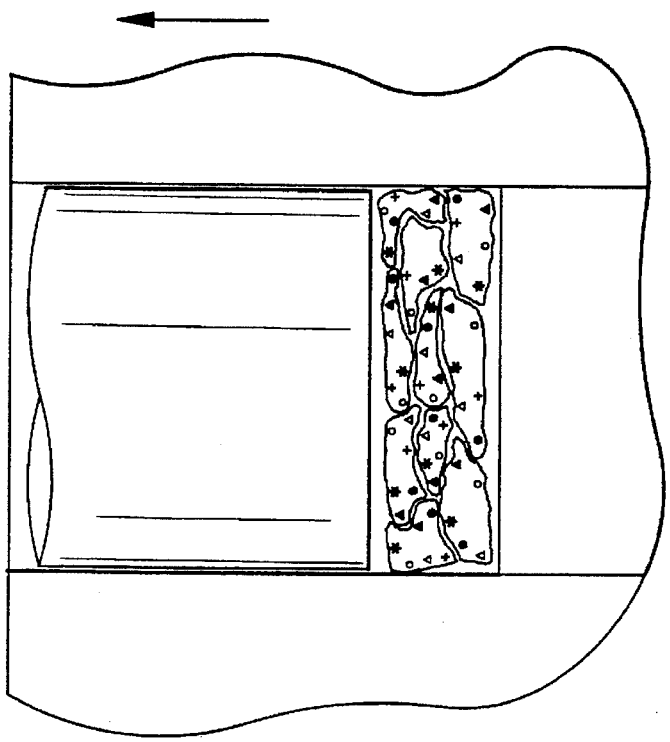
FIG. 4(a) is a schematic representation of a compression die during compression of a table prepared in accordance with the present invention.

FIG. 4(a) shows "microstructurally-fixed," components remaining in place relative to each other, even under compression. Deformation resulting from the force of compression does not force the ingredients out of mixture or cause "clumping." The homogeneity of the mixture is not disturbed as a result of compression. In the photomicrograph of FIG. 2(a) particles of a tablet prepared in accordance with the invention are shown to have relatively the same composition and, thus, the same appearance under the microscope.

FIG. 4(b) shows the compression stroke of the prior art process forcing the components into clumps. This phenomenon reduces the homogeneity. Consequently, particles will be together in a non-homogeneous mixture.

Figure 1:
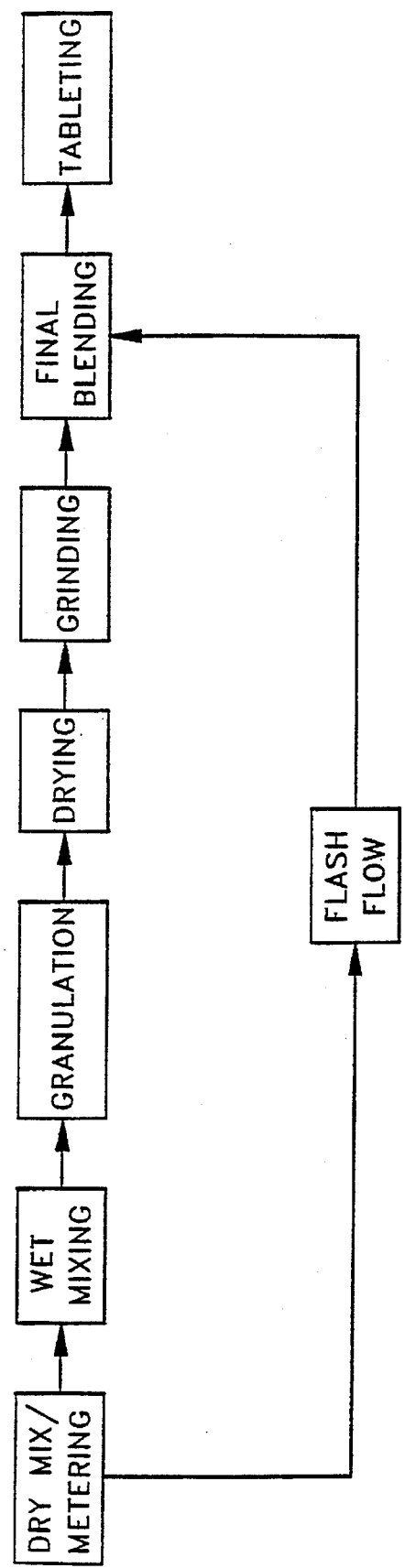
FIG. 1 is a block diagram in which the process and apparatus of the present invention are compared to prior art processes and apparatus.

In prior art processes, the particles are prepared by different methods. FIG. 1 depicts a comparison of the inventive process to a prior art wet granulation method. The prior art wet granulation method has been shown schematically along the uppermost procedure blocks while the process according to the present invention has been shown immediately therebelow in parallel. In wet granulation procedures, individual powder particles are coated and then formed into agglomerates which are called granules. Fusion of the ingredients in prior art procedures depends in large part on compression of the ingredients. In the present invention, fusion of the ingredients in a microstructurally-stabilized mixture is achieved entirely prior to compression.

Referring to FIG. 1, it can be clearly seen that the inventive process eliminates many steps required to prepare the final blend for tabletting in accordance with the prior art wet granulation. Thus, the present invention is a major improvement for preparing compression tablets over wet granulation.

In order to fuse particles together as a dry granulation, dry powders are slugged by compressing in a tablet press having die cavities large enough in diameter to fill quickly and without difficulty. Inaccuracy in the condition of the slug is not important. The slugs are then milled to yield granulation which is again compressed to form a compression tablet. In an alternative dry granulation method, the pressure roll process, a compacted mass is produced by continuous flow through pressure rolls. The compacted sheet or cake falls apart into large aggregates which are screened and then milled for production of granules. Fusion, if it takes place at all, can take place at the precompression stage or at the final compression stage.

Unlike the prior art procedures, fusion in the present invention takes place during flash flow and does not depend on compression. Thus, the manufacturer has controls over the mixture of the ingredients before delivery to the final compression stage. Moreover, additional ingredients can be added and fused with the carrier material without relying on brute force to effect fusion. In fact, tablets made in accordance with the present invention can be formed under compression force significantly reduced from those forces used in the prior art.

As an additional benefit, the tablets made in accordance with the present invention have disintegration interstices which enhance disintegration of the tablets. Referring to FIG. 2(a), one can see that the free form agglomerates are compressed in a "block-to-block" relationship with interstitial voids at intersection of the particle boundaries. These voids provide a ready break point for fracturing the tablet body and propagating its disintegration.

The carrier material can be selected from material which is capable of undergoing both physical and/or chemical changes associated with flash-flow processing. Materials useful as matrices may be chosen from those carbohydrates which are capable of forming free-form agglomerates upon being processed. Maltodextrins are an example of such carrier materials. Maltodextrins include those mixtures Of carbohydrates resulting from hydrolysis of a saccharide feedstock which are described as solids having a DE of less than 45.

The feedstock can also include maltooligo-saccharides produced by selective hydrolysis of cornstarch followed by removal of high and low molecular weight compounds. The general description of malto-oligosaccharides as contemplated herein is set forth in co-pending U.S. application Ser. No. 07/847,595 filed Mar. 5, 1992, now U.S. Pat. No. 5,387,431.

Other materials useful as matrices may be chosen from such classes as sugars or sugar derivatives. The term sugar is meant to include those carbohydrates having a high glucose profile. A high glucose profile means that the carbohydrate has a large number of six-carbon mono and disaccharides as well as other glucose-based oligomers. Mono-, di-, tri- and polysaccharides and their derivatives may be employed. Examples include glucose, sucrose, maltose, lactose, arabinose, xylose, ribose, fructose, mannose, pentose, galactose sorbose, dextrose, sorbitol, xylitol, mannitol, pentatol, maltitol, isomalt, sucralose and mixtures thereof.

Polydextrose is also contemplated for use as a carrier. Polydextrose is a non-sucrose, essentially non-nutritive carbohydrate substitute. It can be prepared through polymerization of glucose in the presence of polycarboxylic acid catalyst and polyols. Generally, polydextrose is known to be commercially available in three forms: polydextrose A and polydextrose K, which are powdered solids, and polydextrose N supplied as a 70% solution. Each of these products also contain some low molecular weight components, such as glucose, sorbitol and certain oligomers. Regarding polydextrose, Applicants incorporate herein the contents of co-pending, U.S. application Ser. No. 07/881,612 filed May 12, 1992, refiled as continuation U.S. application Ser. No. 08/120,171 now issued as U.S. Pat. No. 5,501,858.

Other matrix materials include celluloses and starches and their chemical and biological derivatives. Celluloses, however, are generally added in combination with mono- and disaccharide-based materials because the celluloses are not as easily processed alone using flash-flow techniques.

Flash-flow processing can be accomplished several ways. Flash-heat and flash-shear are two such processes which can be used. In the flash-heat process the feedstock material is heated sufficiently to create an internal flow condition which permits part of the feedstock to move at subparticle level with respect to the rest of the mass and exit openings provided in the perimeter of a spinning head. The centrifugal force created in the spinning head flings the flowing feedstock material outwardly from the head so that it reforms with a changed structure. Inasmuch as the medicinal substance is present at the same time, the substance is fused to the feedstock material as it reforms so that it is substantially dispersed throughout the free-form agglomerate which is produced by the spinning head. The force necessary to separate and discharge flowable feedstock is only the centrifugal force which results in the spinning head. There is no compression whatsoever used to fuse the medicinal substance to the carrier.

One preferred apparatus for implementing a flash heat process is a "cotton candy" fabricating type of machine. The spinning machine used to achieve a flash-heat condition is a cotton candy machine such as the Econo-Floss Model 3017 manufactured by Gold Medal Products Company of Cincinnati, Ohio. Any other apparatus or physical process which provides similar forces and temperature gradient conditions can also be used.

In the flash-shear process, a shearform matrix is formed by raising the temperature in the feedstock material which includes a non-solubilized carrier, such as a saccharide-based material undergoes internal flow upon application of a fluid shear force. The feedstock is advanced and ejected while in internal flow condition, and subjected to disruptive fluid shear force to form multiple parts or masses which have a morphology different from that of the original feedstock.

The multiple masses are cooled substantially immediately after contact with the fluid shear force and are permitted to continue in a free-flow condition until solidified. The medicinal substance is fused to the carrier as it undergoes internal flow, disruption, and reformation as a free-form agglomerate. No compression whatsoever is used to effect fusion.

The flash shear process can be carried out in an apparatus which has means for increasing the temperature of a non-solubilized feedstock and means for simultaneously advancing it for ejection. A multiple heating zone twin screw extruder can be used for increasing the temperature of the non-solubilized feedstock. A second element of the apparatus is an ejector which provides the feedstock in a condition for shearing. The ejector is in fluid communication with the means for increasing the temperature and is arranged at a point to receive the feedstock while it is in internal flow condition. The ejector is preferably a nozzle which provides high pressure ejection of the feedstock material. See co-pending commonly-owned U.S. patent application Ser. No. 965,804 filed Oct. 23, 1992 entitled "Process For Making Shearform Matrix," which is incorporated herein by reference.

Medicinal substances which can be used in the present invention are varied. A non-limiting list of such substances is as follows: antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and anti-thyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

Since a number of bio-affecting agents are heat sensitive, the present invention includes a process step of introducing heat sensitive agents at a point sufficiently proximal the flash-flow process step to reduce exposure of the heat sensitive to prolonged heat conditions. Thus, any heat sensitive agent can be incorporated into a carrier for subsequent ejection and formation of a shear-form matrix product.

Another ingredient which can be included is an oleaginous material such as oleaginous liquid oleaginous flavor or aromatic oil as well as mineral oil, glycerin, polyethylene glycol, and the like. Examples of oleaginous liquids include, without limitation, vegetable oils, fish oils, lard, lanolin, cocoa butter and mixtures thereof. It will be appreciated that those hydrophobic materials which are solid at room temperature can be used provided they are rendered sufficiently liquid to be dispersed within a matrix during processing. Alternatively, in cases where the oleaginous material can be rendered dispersible with preheating without destroying or losing volatile components, such preheating can be employed.

Hydrogenated or partially hydrogenated vegetable oils are useful in the present invention and include materials such as corn oil, canola oil, cottonseed oil, sesame oil, soybean oil, grapeseed oil, sunflower oil, safflower oil, olive oil, peanut oil and the like.

Other ingredients which may be included are fragrances, dyes, sweeteners both artificial and natural, and other additives for assisting in the tabletting process.

For example, fillers may be used to increase the bulk of the tablet to enable formulation to become suitable for compression. Some of the commonly used fillers are calcium sulfate, both dye and di- and tri basic, starge, calcium carbonate, microcrystalline cellulose, modified starches, lactose, sucrose, maintol, and sorbitol.

Other ingredients includes binders which contributes to the ease of compression and general quality of the tablet. Binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Lubricants are also useful in tabletting formulations in order to ease the ejection of the tablet from the die and to prevent sticking of the tablets to the punches and excess wear on dies and punches. Lubricants can include, but are not limited to, the following: magnesium stearate, calcium stearate, zinc stearate, hydrogenated vegetable oils, sterotex, polyoxyethylene, monostearate, talc, polyethyleneglycol, sodium benzoate, sodium lauryl sulfate, magnesium lauryl sulfate and light mineral oil.

Furthermore, disintegrants can be used to enhance the breakability of the compressed tablet in an aqueous environment. The disintegrants can include starch, alginic acid, guar gum, kaolin, bentonite, purified wood cellulose, sodium starch glycolate, isoamorphous silicate, and microcrystalline cellulose.

Another ingredient useful in tabletting are glidants which add to the cohesive matters in order to enhance flow properties by reducing interparticle friction. Glidants which can be used include starch, talc, magnesium and calcium stearate, zinc stearate, dibasic calcium phosphate, magnesium carbonate, magnesium oxide, calcium silicate, and silica aerogels.

Color additives useful in preparing tablets include food, drug and cosmetics (FD&C) colors, drug and cosmetic (D&C) colors, or external drug and cosmetic (Ext. D&C) colors. These colors are dyes, their corresponding lakes, and certain natural and derived colorants. Lakes are dyes absorbed on aluminum hydroxide.

In a preferred embodiment, the present invention is particularly useful in preparing antacid compression tablets. Antacids are conveniently provided in chewable tablet form to provide a convenient method of delivering antacid to the consumer. The chewable form provides an advantage in that the tablet is broken up into granules during chewing and mixed with saliva before swallowing. This renders the tablet antacid formulation a suspension. Active antacid ingredients include but are not limited to the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

Actual tests were conducted to show the efficacy of the present invention when used for the purpose of producing antacid tablets.

EXAMPLE 1

A antacid tablet was prepared in accordance with the present invention in order to compare to prior art antacid tablets made with calcium carbonate. The feedstock for flash flow processing was prepared in accordance with the formula set forth below in Table 1.

TABLE 1

| Ingredient | % Content |
| --- | --- |
| Maltodextrin (MALTRIN M-365) | 42.0% |
| Glycerin | 4.0% |
| Mannitol Powder | 4.0% |
| Calcium Carbonate | 50.0.% |
| | 100.0% |

Materials were premixed and then added to a spinning head spun at about 3,600 rpm. The temperature was set at 125° C. The product appeared as white flakes having a good color quality with no discoloration.

This free-form agglomerate product was then added to a tabletting press in an amount of 95.57% along with 0.05% magnesium stearate, 1.0% talc, 2.5% cornstarch powder, 0.25% high intensity sweetener (aspartame), and 0.18% predistilled oil of peppermint.

The tablets were pressed under pressure of about 9–12 pounds per square inch. The resulting tablets were antacid tablets having good firm product body.

The tablets were cut in half and compared to the popular antacid tablet, TUMS®. The results are shown in FIG. 2(a) and FIG. 2(b). In FIG. 2(a), the cross-section of the tablet prepared in accordance with the present invention is shown. The particles shown therein have consistent bodies which indicates a homogeneous mixture of all compounds throughout the tablet. Furthermore, the particles shown on FIG. 2(a) show clear lines of demarcation at the boundaries thereof which is required for fracture propagation after initial breakage. In FIG. 2(a) the cross-section of the TUMS® tablet shows that the ingredients are non-homogeneous by mixed. The ingredients appeared to be in clumps.

EXAMPLE 2

A feedstock for making an antacid tablet in accordance with the present invention was prepared using the composition set forth below.

TABLE 2

| Ingredient | % Content |
| --- | --- |
| Maltodextrin (MALTRIN M-365) | 44.7% |
| Glycerin | 5.0% |
| High Intensity Sweetener (Acesulfame-K) | 0.3% |
| Calcium Carbonate | 50.0% |
| | 100.0% |

The glycerin and calcium carbonate were initially combined and blended before adding Acesulfame K and continuing blending for about 1 minute. This mixture was then added to an industrial mixing machine (i.e., a Hobart mixer) and the maltodextrin was added and mixed for about 5 minutes.

The feedstock thus prepared was introduced into a spinning head operated at 3600 rpm at an operating temperature of 125° C. (actual temperature of feedstock 124° C.) and spun continuously until all the material had been processed.

The feedstock resulted in small white flakes and was tested to determine the coherency and the size distribution of the product. The results of the product in terms of size distribution has been reported hereinbelow in Table 8.

EXAMPLE 3

A further example of a feedstock material was prepared in accordance with the compositions set forth below.

TABLE 3

| Ingredient | % Content |
| --- | --- |
| Maltodextrin (MALTRIN M-365) | 44.7% |
| Glycerin | 4.0% |
| Lecithin | 1.0% |
| High Intensity Sweetener (Acesulfame-K) | 0.3% |
| Calcium Carbonate | 50.0% |
| | 100.0% |

The feedstock was processed as in Example 1 in the flash flow apparatus which was run at a speed of 3600 rpm at a temperature setting of 135° C. (actual temperature of flash flow material 120° C.). The product was screen tested as in Example 2, and the results are reported in Table 8.

EXAMPLE 4

The third example of feedstock for tabletting was prepared as in Example 1 using the following composition.

TABLE 4

| Ingredient | % Content |
| --- | --- |
| Maltodextrin (MALTRIN M-365) | 39.7% |
| Glycerin | 4.0% |
| Mannitol Powder | 5.0% |
| Lecithin | 1.0% |
| High Intensity Sweetener (Acesulfame-K) | 0.3% |
| Calcium Carbonate | 50.0% |
| | 100.0% |

The machine was operated at 3600 rpm at a temperature setting 125° C. (actual temperature of flash flow material 120° C.).

The resulting product was a light particulate which was screen tested and the results are reported in Table 8.

EXAMPLE 5

A further feedstock was prepared in accordance with the procedure set forth in Example 1 in accordance with the following composition.

TABLE 5

| Ingredient | % Content |
| --- | --- |
| Maltodextrin (MALTRIN M-365) | 41.7% |
| Glycerin | 4.0% |
| Mannitol Powder | 4.0% |
| High Intensity Sweetener (Acesulfame-K) | 0.3% |
| Calcium Carbonate | 50.0% |
| | 100.0% |

The flash flow apparatus was operated at 3600 rpm at a temperature setting of 143° C. (actual temperature flash flow feedstock 142° C.).

The product resulting from the above-procedure took the form of granules and small white flakes with a high quality of taste. The product was screen tested and the results are reported in Table 8.

EXAMPLE 6

Yet another free form agglomerate was prepared for tabletting an antacid tablet by the process as set forth in Example 1 using the following composition:

TABLE 6

| Ingredient | % Content |
| --- | --- |
| Maltodextrin (MALTRIN M-365) | 41.7% |
| Glycerin | 4.0% |
| Mannitol Powder | 4.0% |
| High Intensity Sweetener (Acesulfame-K) | 3.0% |
| Calcium Carbonate | 50.0% |
| | 100.0% |

The flash flow apparatus was run at 3600 rpm and at a temperature setting of 135° C. (actual temperature of the flash flow material 134° C.).

The product had an appearance of medium fine granular flakes having a nice white appearance and excellent taste.

The product was subjected to screen testing and the results are reported in Table 8.

EXAMPLE 7

Yet another example was prepared exactly as set forth in Example 5 hereinabove and the results of the screen test are reported in Table 8.

TABLE 8

| Mesh Size - in Microns | EXAMPLE 2 Percent Particle | EXAMPLE 3 Percent Particle | EXAMPLE 4 Percent Particle | EXAMPLE 5 Percent Particle | EXAMPLE 6 Percent Particle | EXAMPLE 7 Percent Particle |
|---|---|---|---|---|---|---|
| 2000 | 5.8% | 1.6% | 9.7% | 3.6% | 3.8% | 3.4% |
| 420 | 80.1% | 57.00% | 71.9% | 64.8% | 82.4% | 71.9% |
| 250 | 11.2% | 24.2% | 10.9% | 22.3% | 11.9% | 14.4% |
| 180 | 2.1% | 9.7% | 4.1% | 6.6% | 1.4% | 5.4% |
| 150 | .29% | 1.75% | 2.2% | 1.8% | .2% | 3.3% |

Discussion of Table 8

The data reported in Table 8 demonstrates the uniformity of particles produced as a result of the present invention and the virtual elimination of fines normally present in tabletting processes. In particular, a quick review of the particle sizes resulting from the flash flow procedures employed in Examples 2–7 show that there are virtually no particles produced which are course, i.e., in the range of 2000 microns, or in the range of fine particles (at about 150 microns).

The majority of particles resulting from the flash flow process pass through the first screen which has a mesh size of 2000 microns and are retained on screens which have a mesh size of 420 microns and 250 microns. These particles are ideal for feeding into tabletting dies. They are easily moved by machine and provide optimum flowability.

Thus, as a result of the present procedure particles are produced with a high predictability of size. A concomitant benefit is the virtual elimination of fines. The size distribution is within parameters which are readily usable for tabletting. The total number of fines are well below 5%, and, generally less than 1% of the product.

As a consequence of the particle size predictability, the skilled artisan can readily engineer particle size for the tablet requirements. This is important to obtain optimum characteristics of the resulting product, but also to use machines which require different ranges of particle sizes because of, among other things, the feed mechanisms associated therewith.

Other compression considerations include compression force, dwell timing speed, etc. The particles prepared for tabletting in accordance with the present invention are ideally suited for preparation of compression tablets such as antacids. The particles are "fluffier" in appearance and shape so that deformation and compaction to a tablet is easily achieved under relatively low compression forces.

EXAMPLE 9

Actual antacid tablets were then prepared from feedstock prepared with different compositions. In this Example, the particulate was prepared in accordance with the following composition.

TABLE 9

| Ingredient | % Content |
|---|---|
| Maltodextrin (MALTRIN M-365) | 42% |
| Glycerin | 4% |
| Mannitol Powder | 4% |
| Calcium Carbonate | 50% |
| | 100% |

The feedstock was processed at 3600 rpm at a temperature setting of 140° C. The product appeared as white flakes.

These antacids formula flakes where then added to a tabletting press at a rate of 95.57% flake, 0.5% magnesium stearate, 1.0% talc, 2.5% corn starch, 0.25% aspartame and 0.18% predistilled liquid flavor peppermint.

Figure 5:
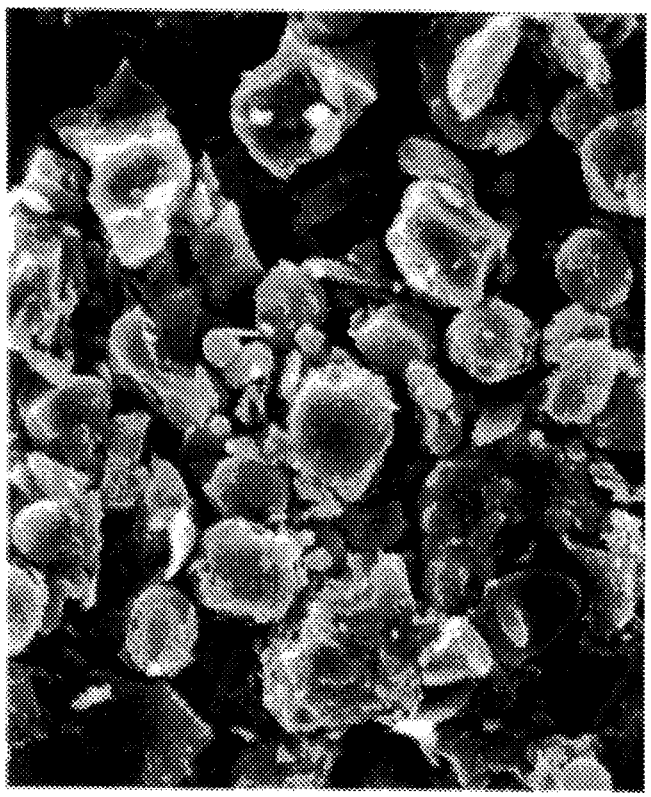
FIG. 5 is a photomicrograph of a compression tablet taken at 1,000 magnification of a tablet prepared in accordance with the present invention.

The resultant tablet was a highly desirable antacid tablet which had good texture and flavor. An inspection of the cross section of the tablet showed a homogeneous mixture of compacted free-form aggregates as shown in FIG. 5.

EXAMPLE 10

In this Example, an antacid tablet was prepared using dihydroxyaluminum sodium carbonate, $Al(OH)_2OOCONa$. The free form aggregates were prepared from the following composition.

TABLE 10

| Ingredient | % Content |
|---|---|
| Dihydroxyaluminum Sodium Carbonate | 22% |
| Medium Chain Triglycerides (MCT) | 5% |
| Maltodextrin | 73% |
| | 100% |

Dihydroxyaluminum sodium carbonate (DASC) and medium chain triglycerides were mixed followed by blending in the maltodextrin until the entire combination was powdered. The feedstock was then processed in a flash flow spinning machine at 125° C.–130° C. at 3600 rpm. The resulting product had excellent white color and a consistent morphology.

The particles prepared by flash flow processing was then combined with 0.5% magnesium stearate, 1.5% talc, 1% corn starch, 0.3% aspartame, 0.25% redistilled liquid flavor peppermint, and 0.25% spray dried peppermint. The combination was introduced to a tabletting press and compressed to form tablets.

The end tablets had excellent taste and firmness, and did not break upon handling. A cross section of the tablet is shown at 1,090 magnification at FIG. 6a. From viewing the photomicrograph at 6a, one can see that the compressed tablet had a homogeneous cross sectional texture.

A comparison was taken of dihydroxyaluminum sodium carbonate tablets available commercially as Rolaids® antacid tablet made and sold by the Warner Lambert Company. The results are shown at FIG. 6(b). Comparison of the two photomicrography show that the Figure at 6(b) depicts a non-homogeneous continuum in the cross-sectional target area. This is dramatic evidence of not only the efficiency of the present invention but the effectiveness of providing a homogeneous mixture in the end product.

MINT EXAMPLES

Another particulate material was prepared in accordance with the present invention for making compression tablets by combining ingredients set forth in the following Mint Table.

MINT TABLE

| Ingredient | % Content |
| --- | --- |
| Fructose | 23% |
| Maltodextrin (Dri Sweet 42) | 23% |
| Powdered Sugar | 49% |
| Citric Acid | 3% |
| Medium Chain Triglycerides (NEDBEE M-5) | 2% |
| | 100% |

The above composition was spun at 3900 rpm at a temperature setting of 145° C. (actual temperature 131° C.). The product produced thereby was produced moderately slowly and resulted in white granules.

The formulation set forth above was used to make mint tablets. In particular, the free flow agglomerates prepared as above were mixed at a rate of 97.55% with magnesium stearate at 1.5%, corn starch at 0.8%, cherry flavoring at 0.6%, Red #40 Lake Coloring at 0.1% and Syloid 244 at 0.25%. The resulting tablets had excellent flavor with a sour note which had good organoleptic balance.

Another tablet was prepared using the mint formulation prepared in free form aggregate as set forth above in an amount of 97.4%, magnesium stearate in an amount of 1.5%, orange flavoring at 0.8%, orange coloring at 0.25% and Syloid 244 at 0.25%. The tablets had good flavor and balanced sourness.

Finally, an additional tablet was prepared using 97.5% of the free form aggregate formed as set forth above, 1.5% magnesium stearate, 0.5% lemon lime flavoring, 0.25 #5 Lake Coloring, and 0.25% Syloid 244. The resulting tablet was easily prepared and had good organoleptic balance and flavor.

LOW-CAL MINT

A low-cal free form aggregate was prepared in accordance with the composition set forth below.

LOW-CAL MINT TABLE

| Ingredient | % Content |
| --- | --- |
| Polydextrose | 51.25% |
| Calcium Carbonate | 40.00% |
| Glycerin | 2.00% |
| Medium Chain Triglycerides | 2.00% |
| Mannitol | 4.00% |
| Lecithin | 0.75% |
| | 100.00% |

The above mixture was processed at 3900 rpm at a temperature setting of 140° C. (the temperature of the flash flow material was 133° C.). The resulting product was a light fluffy cream-colored flake.

Tablets were produced from the free form aggregate produced in accordance with the process set forth above. By inclusion in the tabletting mixture at a rate of 97.6% along with #5 Lake Coloring at 0.2%, sodium chloride at a rate of 0.6%, peppermint oil at rate of 0.2%, diacetal at a rate of 0.06%, and aspartame at a rate of 0.3% and magnesium stearate at a rate of 1.0%.

The resulting tablet had excellent flavor and fractured readily under medium chew pressure.

ACETAMINOPHEN EXAMPLE

A free form aggregate was formed from a feedstock which was prepared in accordance with the following composition.

ACETAMINOPHEN TABLE

| Ingredient | % Content |
| --- | --- |
| Acetaminophen (APAP) | 50.0% |
| Sorbitol | 4.0% |
| Malti-sorbo (Roquette) | 17.5% |
| Maltodextin (MALTRON 365) | 17.5% |
| Lecithin | 1.0% |
| Medium Chain Triglyceride (NEOBEEM 5) | 3.0% |
| Polyethylene Glycol | 2.0% |
| Dicalcium Phosphate | 5.0% |
| | 100.0% |

The above mixture was processed on a flash flow machine at 3600 rpm at a temperature setting of 140° C. (temperature of flash flow material 123° C.). White fluffy granules resulted which were used in tabletting.

The tablets were prepared using 97% of the drug-bearing free form aggregates set forth above at a rate of 97% along with 2% magnesium stearate and 1% talc.

The resulting product represents a delivery system for delivery of an active ingredient which was not subjected to neither high temperature processing nor high compression during production.

Thus, while there have been what are presently to believed to be the preferred embodiments of the present invention, those skilled in the art will realize that other and further modifications can be made to the invention without departing from the true spirit of the invention, such further and other modifications are intended to be included herein within the scope of the appended claims.

What is claimed:

1. A method of making a solid comestible comprising:
   a. forming deformable particles, substantially all said particles having a particle size of from 150 to 2000 microns wherein a majority of said particles pass through a screen having a mesh size of 2000 microns and are retained on screens having a mesh size of 420 microns and 250 microns, said particles being compressible in a die and punch tabletting machine by subjecting a feedstock comprising a carrier material, selected from the group consisting of maltodextrin, maltooligosaccharides, polydextrose, sugars, and combinations thereof, to flash-flow processing; and
   b. compressing said particles in a die and punch tabletting machine sufficiently to form a comestible compression unit which possesses a rigid structure and a surface having a hardness which resists penetration and deformation.

2. The method of claim 1 wherein said flash-flow is provided by high speed spinning in a spinning head in which said feedstock is subjected to heat and shear sufficient to create flash-flow and which discharges said particles during spinning.

3. The method of claim 1 wherein said flash-flow is provided by heating said feedstock in a solubilized condition sufficiently to provide internal flow conditions, and subjecting said feedstock to disruptive fluid shear force to the form said particles.

4. The method of claim 1 wherein said feedstock comprises a carrier material which undergoes morphological transformation during flash-flow processing to produce said particles.

5. The method of claim 4 wherein said feedstock further comprises an additive which, during flash-flow processing, is mixed and microstructurally stabilized in said particles.

6. The method of claim 5 wherein said additive is selected from the group consisting of medicaments, dyes, fragrances, sweeteners, flavors, fillers, binders, lubricants, disintegrants, and mixtures thereof.

7. The method of claim 6 wherein said additive is a medicament selected from the group consisting of antitussives, antihistamines, decongestants, alkaloids, mineral supplements, laxatives, vitamins, antacids, ion exchange resins, anti-cholesterolemics, anti-lipid agents, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psycho-tropics, antimanics, stimulants, gastrointestinal agents, sedatives, antidiarrheal preparations, anti-anginal drugs, vasodialators, anti-hypertensive drugs, vasoconstrictors, migraine treatments, antibiotics, tranquilizers, anti-psychotics, antitumor drugs, anticoagulants, antithrombotic drugs, hypnotics, anti-emetics, anti-nauseants, anti-convulsants, neuromuscular drugs, hyper- and hypoglycemic agents, thyroid and anti-thyroid preparations, diuretics, antispasmodics, uterine relaxants, mineral and nutritional additives, antiobesity drugs, anabolic drugs, erythropoietic drugs, antiasthmatics, cough suppressants, mucolytics, anti-uricemic drugs and mixtures thereof.

8. The method of claim 7 wherein said medicament is an antacid.

9. The method of claim 1 wherein said compression is performed without requirement for a processing aid.

10. The method of claim 1 wherein said carrier material is selected from the group consisting of maltodextrin, maltooligosaccharides, polydextrose and combinations thereof.

11. The method of claim 10 wherein said carrier material is maltodextrin.

12. The method of claim 1 wherein said particles are flowable.

13. The method of claim 12 wherein there are less than 5% fines in said particles.

14. The method of claim 13 wherein there are less than 1% fines.

15. The method of claim 1 wherein said deformable particles comprise ingredients which are microstructurally stabilized against migration out of said particles.

* * * * *